United States Patent [19]

Poppendiek

[11] 4,236,403
[45] Dec. 2, 1980

[54] MEANS AND TECHNIQUES USEFUL IN ESTABLISHING R VALUES IN INSULATION

[75] Inventor: Heinz F. Poppendiek, La Jolla, Calif.

[73] Assignee: Thermonetics Corporation, San Diego, Calif.

[21] Appl. No.: 915,524

[22] Filed: Jun. 14, 1978

[51] Int. Cl.³ .............................................. G01N 25/18
[52] U.S. Cl. .................................................... 73/15 A
[58] Field of Search .................................. 73/15 A, 11

[56] References Cited

U.S. PATENT DOCUMENTS 2,878,669  3/1959  Knudson et al. .................... 73/15 A

OTHER PUBLICATIONS

Hody et al., "Direct in situ Measurement of Thermal Insulation Quality Underwater", IEEE Int. Conf. on Eng. in The Ocean Environment 9/1973, pp. 133–136.

*Primary Examiner*—Herbert Goldstein

[57] ABSTRACT

The R value of heat insulation already in situ in a wall of a building structure which has already been subjected to climatic hot and cold conditions is established under transient conditions that exist over a 24 hour period by establishing a first series of values, each representative of the difference in temperature between the inner and outer wall at successive times during such 24 hour period and simultaneously establishing a second series of values, each representative of the heat flux into or out of the wall at said same successive times, and combining said first and said second series of values to obtain said R value.

2 Claims, 4 Drawing Figures

MEANS AND TECHNIQUES USEFUL IN ESTABLISHING R VALUES IN INSULATION

The present invention relates to means and techniques useful in establishing so called R factors of thermal insulation, which has already been installed as a permanent part of existing building structures that have already been subjected to various climatic conditions, such as being heated by the sun during the day and thereafter cooled during the night.

An object of the present invention is to provide means and techniques useful in establishing R values of insulation under transient conditions.

Another objects of th present invention is to provide means and techniques useful in establishing R values of insulation by observing and evaluating transient temperature and related transient heat flow fields during cyclical heating and cooling conditions.

IN THE DRAWINGS

The so called R value of thermal insulation is readily established in the laboratory when steady state conditions exist and the prior history of the insulation is such that effects of prior heating or cooling of the insulation have already stabilized.

Figure 1:
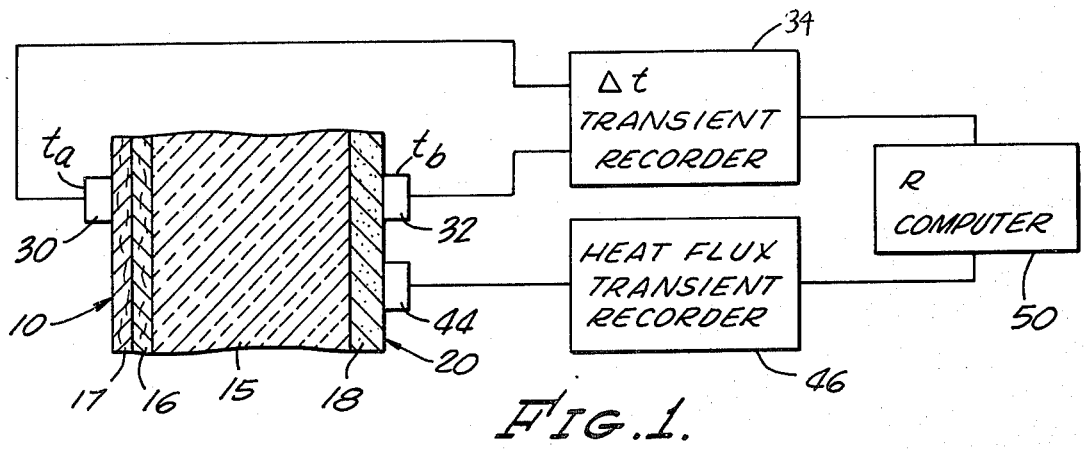
FIG. 1 illustrates a system embodying features of the present invention.

These ideal laboratory conditions do not exist when insulation already exists in situ between the walls of existing building structures which have already undergone numerous day-night heating cycles during which the outside temperature $t_a$ at the outside wall 10 in FIG. 1 changes from a low temperature during the night to a high temperature during the day while the inside temperature $t_b$ at the inside wall 20 may remain substantially constant.

In FIG. 1 the thickness of the heat insulation 15 may, for example, be approximately three and one half inches, the width of a conventional stud, and the outer wall 10 may comprise an inner layer of sheathing 16 and an outer layer of siding 17 while the inner wall 18 may consist of gypsum board.

Figure 2:
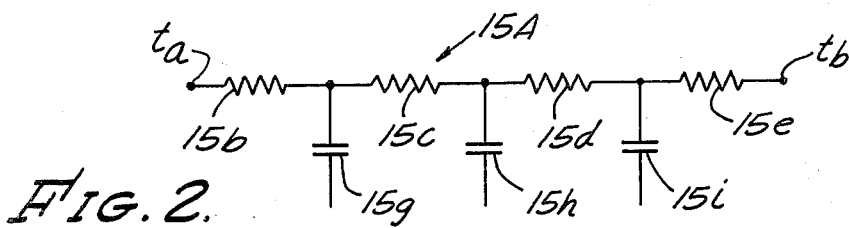
FIG. 2 represents an equivalent circuit of heat insulation.

Depending upon cyclical temperature conditions, there may be at any one particular time a heat flow from the outside wall 10 into the insulation 15 as during the day when the building wall structure is being heated by the effects of the sun and, conversely, there may be a heat flow in the opposite direction when the ouside temperature during the night falls. The insulation stores heat during the day and then discharges heat to the outside during the night. The electrical analog of the insulation may be illustrated in FIG. 2, wherein 15A represents an equivalent electrical circuit consisting of a series of series connected resistors 15a–15e which interconnect a series of shunt connected capacitors 15g, 15h, 15i. Depending upon the present and prior differences in temperature $t_a$–$t_b$ (which may represent voltage), there is either a charging or a discharging of the equivalent capacitors in accordance with well recognized electrical circuit theory and operation. Thus, one attempting to establish the R value of the insulation using convention methods would obtain erroneous values because of the unknown "charging" or "discharging" conditions of the insulation.

In accordance with the present invention, measurement are made over a period of time such as, for example, a 24 hour interval, i.e., during one cycle, and measurements taken at spaced time intervals during such cycle are averaged to establish the R value.

The system is instrumented as shown in FIG. 1. The difference in inside and outside temperatures referred to as delta t is measured using a series of thermo cold and hot junctions, 30 and 32, respectively, and their combined outputs is applied to a clock driven recorder 34 which produces the difference in temperature $(t_b-t_a)$ recording 40 on recording paper 42.

Also, a heat flux sensor 44 is mounted on either one of the walls 17, 18 and its output is applied to the heat flux transient recorder 46 which may use, on a time sharing basis, or otherwise the same recording paper 42 to produce the recording 48 representative of the heat flux passing through such wall.

The heat flux is the heat flow in BTU per hour divided by unit area and is equal to $(t_b-t_a)$ divided by R. R has the units of hour, foot square, degrees Fahrenheit divided by BTU. R may also be defined by L (thickness of wall) divided by k, its effective thermal conductivity, i.e., R equals L divided by k.

Figure 3:
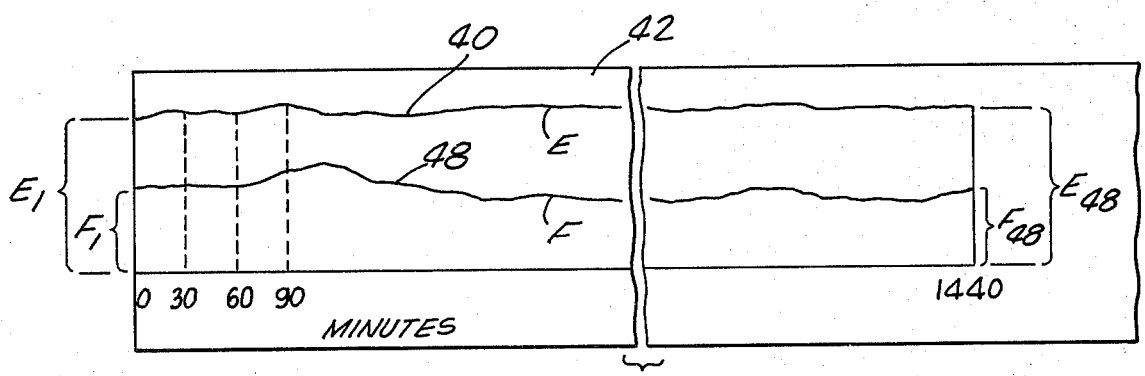
FIG. 3 illustrates a recording obtained in the use of FIG. 1

The temperature difference and heat flow readings E and F may be evaluated at successive one-half hour intervals during a 24 hour period to obtain forty-eight readings of temperature difference and heat flux $E_1$–$E_{48}$ and $F_1$–$F_{48}$, respectively, as indicated in FIG. 3 and such readings may be obtained manually from the graph itself or may be applied to a computer 50 which performs the same mathematical operation, namely:

$$R = \frac{E_1 + E_2 + E_3 \ldots + E_{48}}{F_1 + F_2 + F_3 \ldots + F_{48}}$$

It can be demonstrated mathematically that this method truly results in a true meaningful value of R, the same as that which would be established under ideal laboratory steady state conditions where, as usual, the effects of any prior heating and/or cooling are nullified before an attempt is made to establish the true value R. Indeed, actual tests have verified this to be so.

Figure 4:
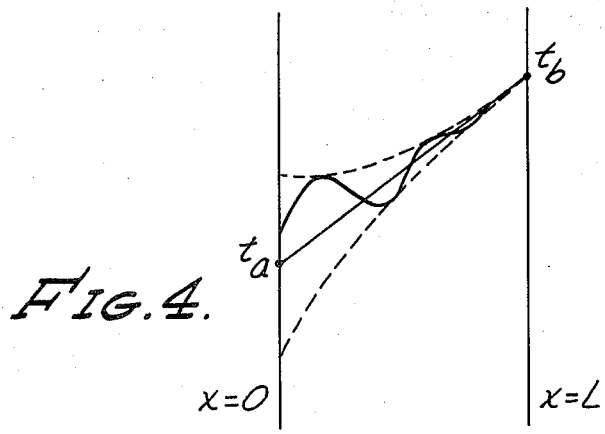
FIG. 4 illustrates temperature variations under transient conditions.

Such mathematical anaylsis may be represented graphically in FIG. 4 where the wall extends from X equals zero to X equals L and the temperature variation over a 24 hour period is the composite of the straight line 60A and the sinusoidal variation 60B whose envelope is defined by the dotted lines 62, 63. This sinusoidal variation 60B is centered about the line 60A with positive and negative values of the sinusoid extending above and below the line and indeed averaging out to zero over a complete 24 hour cycle so that the straight line 60A itself is representative of measurements made under steady state heat transfer conditions.

I claim:

1. A method for establishing the R value of heat insulation which is located in situ in a wall of a building structure that is subjected to varying temperature conditions over a cyclical period during which heat flow through said wall is first in one direction and then later in an opposite direction which is opposite to said first direction, establishing a first series of values representing the difference in temperature at different successive times during such cyclical period when said heat flow is in said one direction and in said opposite direction, establishing a second series of values representing heat flow in the wall at said same difference successive times in said one direction and in said opposite direction, and combining said first and said second series of values to establish said R value.

2. A method as set forth in claim 1 in which said first and second series of values are averaged.

* * * * *